United States Patent
Kawai

(10) Patent No.: US 9,709,522 B2
(45) Date of Patent: Jul. 18, 2017

(54) SOLID ELECTROLYTE GAS SENSOR ELEMENT AND GAS SENSOR

(71) Applicant: Masashi Kawai, Miyoshi (JP)

(72) Inventor: Masashi Kawai, Miyoshi (JP)

(73) Assignee: Toyota Jidosha Kabushiki Kaisha, Toyota-shi, Aichi-ken (JP)

(*) Notice: Subject to any disclaimer, the term of this patent is extended or adjusted under 35 U.S.C. 154(b) by 44 days.

(21) Appl. No.: 14/412,473

(22) PCT Filed: Sep. 10, 2013

(86) PCT No.: PCT/IB2013/001960
§ 371 (c)(1),
(2) Date: Jan. 2, 2015

(87) PCT Pub. No.: WO2014/057322
PCT Pub. Date: Apr. 17, 2014

(65) Prior Publication Data
US 2015/0204812 A1    Jul. 23, 2015

(30) Foreign Application Priority Data

Oct. 9, 2012  (JP) .................................. 2012-224215

(51) Int. Cl.
 *G01N 27/407*  (2006.01)
(52) U.S. Cl.
 CPC ..... *G01N 27/4072* (2013.01); *G01N 27/4077* (2013.01)
(58) Field of Classification Search
 CPC ........... G01N 27/4077; G01N 27/4072; G01N 27/4071; G01N 27/4073; B32B 18/00;
(Continued)

(56) References Cited

U.S. PATENT DOCUMENTS 5,800,689 A   9/1998  Hori et al.
6,797,138 B1 * 9/2004  Detwiler ............ G01N 27/4071
                                                    204/424

(Continued)

FOREIGN PATENT DOCUMENTS

JP       8-240559      9/1996
JP     2007-248357     9/2007

(Continued)

OTHER PUBLICATIONS

U.S. Appl. No. 15/617,115, filed Jun. 8, 2017.

*Primary Examiner* — Xiuyu Tai
(74) *Attorney, Agent, or Firm* — Finnegan, Henderson, Farabow, Garrett & Dunner, LLP

(57) ABSTRACT

A gas sensor element includes: a solid electrolyte body; a target gas chamber; a reference gas chamber; a first electrode coming into contact with the solid electrolyte in the target gas chamber; a second electrode coming into contact with the solid electrolyte body in the reference gas chamber so as to hold the solid electrolyte body between the first electrode and the second electrode; a diffusion layer arranged to come into contact with the solid electrolyte body and configured to deliver the target gas to the target gas chamber; and a shielding layer arranged to come into contact with the diffusion layer so as to arrange the diffusion layer between the solid electrolyte body and the shielding layer. At least one of the solid electrolyte body and the shielding layer is provided with a concave section depressed from an interface side with the diffusion layer.

8 Claims, 7 Drawing Sheets

(58) Field of Classification Search
CPC . C04B 35/119; C04B 35/443; C04B 35/4885; C04B 35/62635; C04B 35/62655; C04B 35/63416; C04B 2235/3244; C04B 2235/3246; C04B 2235/5454; C04B 2235/6021; C04B 2235/602
See application file for complete search history.

(56) References Cited

U.S. PATENT DOCUMENTS

| | | | |
|---|---|---|---|
| 2008/0094079 A1* | 4/2008 | Suzuki | G01N 27/407 324/713 |
| 2009/0050493 A1 | 2/2009 | Saji et al. | |
| 2010/0031731 A1 | 2/2010 | Kawase et al. | |
| 2011/0094883 A1* | 4/2011 | Ito | G01N 27/4077 204/429 |

FOREIGN PATENT DOCUMENTS

| | | |
|---|---|---|
| JP | 2009-36608 | 2/2009 |
| JP | 2010-038794 | 2/2010 |
| JP | 2011-247790 | 12/2011 |
| JP | 2012-93330 | 5/2012 |

* cited by examiner

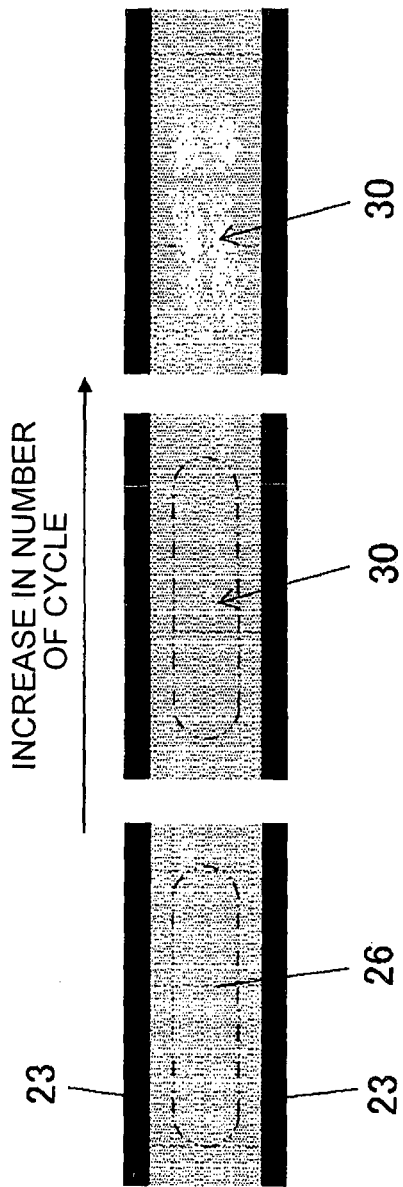

SOLID ELECTROLYTE GAS SENSOR ELEMENT AND GAS SENSOR

CROSS-REFERENCE TO RELATED APPLICATIONS

This application is a national phase application of International Application No. PCT/IB2013/001960, filed Sep. 10, 2013, and claims the priority of Japanese Application No. 2012-224215, filed Oct. 9, 2012, the content of both of which is incorporated herein by reference.

BACKGROUND OF THE INVENTION

1. Field of the Invention

The present invention relates to a gas sensor element for detecting a specific gas concentration in a measured gas (target gas) and a gas sensor using the same.

2. Description of Related Art

In an exhaust system of an internal combustion engine and the like for a vehicle, a gas sensor is disposed to detect a specific gas concentration (oxygen concentration, for example) in a target gas, such as an exhaust gas (see Japanese Patent Application Publication No. 08-240559 (JP 08-240559 A), for example). Such a gas sensor houses a gas sensor element that has, for example, an oxygen ion conductive solid electrolyte body, a measuring electrode and a reference electrode that are respectively provided in one surface and the other surface of the solid electrolyte body, and a diffusion layer that covers the measuring electrode and allows the target gas to permeate therethrough.

Among conventional gas sensor elements, the element is configured such that an outer surface thereof comes into contact with the exhaust gas. However, water vapor contained in the exhaust gas is condensed and becomes water drops when the internal combustion engine is started, and there is a case where the water drops are splashed together with the exhaust gas on the element. Here, the gas sensor element is used under a heated condition at a high temperature so that the solid electrolyte body is activated. Accordingly, a significant thermal shock is applied to the element due to adhesion of the water drops, which possibly causes water-induced cracking. In addition, a poisoning substance that adversely affects sensing performance may be contained in the exhaust gas. Therefore, JP 08-240559 A and Japanese Patent Application Publication No. 2012-93330 (JP 2012-93330 A) disclose an oxygen concentration detector in which a surface protective layer with water repellency is provided on an outer side of the element and porous layers are laminated to prevent heat transfer and to catch the poisoning substance.

Although techniques in the above documents presuppose use of the protective layer with water repellency, there is a possibility that the water repellency cannot be maintained sufficiently with time. In other words, when constituent particles of the surface protective layer are coated with the poisoning substance (a particulate oxide, for example) that is contained in the exhaust gas, the water repellency thereof is possibly degraded. Furthermore, the function of the porous layer to catch the poisoning substance becomes ineffective for the poisoning substance that is dissolved in a liquid (water, for example).

Fuel is basically made of hydrocarbons but also contains various impurities such as nitrides, water, mineral elements, and metallic elements derived from an additive. These impurities turn into a composite/mixed compound (the poisoning substance) that adversely affects defecting performance of the gas sensor and that generally exists in the exhaust gas. The above poisoning substance and water form a complex system in an exhaust system of the internal combustion engine due to factors such as the structure, combustion control, and a property of the fuel. In order to solve the above, plural inventions have reported improvement of the protective layer by taking wetness and poisoning into account. However, a sufficient effect has not been achieved.

SUMMARY OF THE INVENTION

The present invention provides a gas sensor element that exhibits superior poisoning resistance against a poisoning substance that is dissolved in a liquid and then enters the inside of the gas sensor element and maintains sensor performance in an initial period, and also provides a gas sensor using the same.

The gas sensor element according to a first aspect of the present invention is the gas sensor element for detecting a concentration of a target gas. The gas sensor element includes: a solid electrolyte body; a target gas chamber to which the target gas is introduced; a reference gas chamber to which a reference gas as a basis for a concentration of the target gas s introduced; a first electrode provided in the target gas chamber to come into contact with the solid electrolyte; a second electrode provided in the reference gas chamber to come into contact with the solid electrolyte body, the second electrode being provided to hold the solid electrolyte body between the first electrode and the second electrode; a diffusion layer arranged to come into contact with the solid electrolyte body and configured to deliver the target gas to the target gas chamber; and a shielding layer arranged to come into contact with the diffusion layer so as to arrange the diffusion layer between the solid electrolyte body and the shielding layer. At least one of the solid electrolyte body and the shielding layer is provided with a concave section depressed from a surface coming into contact with the diffusion layer.

According to the first aspect, because the soluble poisoning substance that is contained in the exhaust gas can be caught in the concave section that is provided in a layer that comes into contact with the diffusion layer at an upper layer or a lower layer thereof, it is possible to remove the influence of the target gas that responds to the electrode on the atmosphere the electrode. Accordingly, deterioration with time hardly occurs.

In the first aspect, when a target gas take-in side that takes in the target gas is seen from the target gas chamber in a plan view, and the length of a wall surface of the target gas chamber that faces the target gas take-in side is set as a chamber width, a range of the concave section in a direction of the chamber width may contain a range in the chamber width.

According to the above aspect, the poisoning substance passes through a diffusion area with the concave section before reaching the target gas chamber. Therefore, a probability of the poisoning substance that passes through the diffusion layer to be caught in the concave section before reaching the target gas chamber is increased.

In the above aspect, a wall surface of the concave section may be perpendicular to an interface thereof with the diffusion layer.

In the above aspect, because a three-phase interface is formed, a probability of the poisoning substance to be caught is further increased.

The gas sensor according to a second aspect of the present invention includes the gas sensor element according to the first aspect.

According to the second aspect, it is possible to obtain an effect achieved by the gas sensor element according to the first aspect.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIGS. 1A and 1B show an embodiment of the present invention in which FIG. 1A is a perspective plan view for showing a structure of a gas sensor element and FIG. 1B is a cross-sectional view taken along the line IB-IB of FIG. 1A;

FIGS. 3A and 3B show the embodiment of the present invention in which FIG. 3A is a plan view for showing a structure of a test piece and FIG. 3B is a cross-sectional view taken along the line IIIB-IIIB of FIG. 3A;

FIG. 4A shows a surface analysis result of the test piece of FIGS. 3A, 3B by an EPMA, and FIG. 4B shows a state of deposition of the poisoning element in the test piece of FIGS. 3A, 3B;

FIGS. 5A and 5B show the embodiment of the present invention in which FIG. 5A is a perspective plan view for showing the structure of the gas sensor element according to a first modification and FIG. 5B is a cross-sectional view taken along the line VB-VB of FIG. 5A;

FIGS. 7A and 7B show the embodiment of the present invention in which FIG. 7A is a perspective plan view for showing the structure of the gas sensor element according to a second modification and FIG. 7B is a cross-sectional view taken along the line VIIB-VIIB of FIG. 7A; and FIGS. 8A and 8B show the embodiment of the present invention in which FIG. 8A is a perspective plan view for showing the structure of the gas sensor element according to a third modification and FIG. 8B is a cross-sectional view taken along the line VIIIB-VIIIB of FIG. 8A.

DETAILED DESCRIPTION OF EMBODIMENTS

A description will be made on an embodiment of the present invention with reference to the accompanying drawings.

Figure 1A:
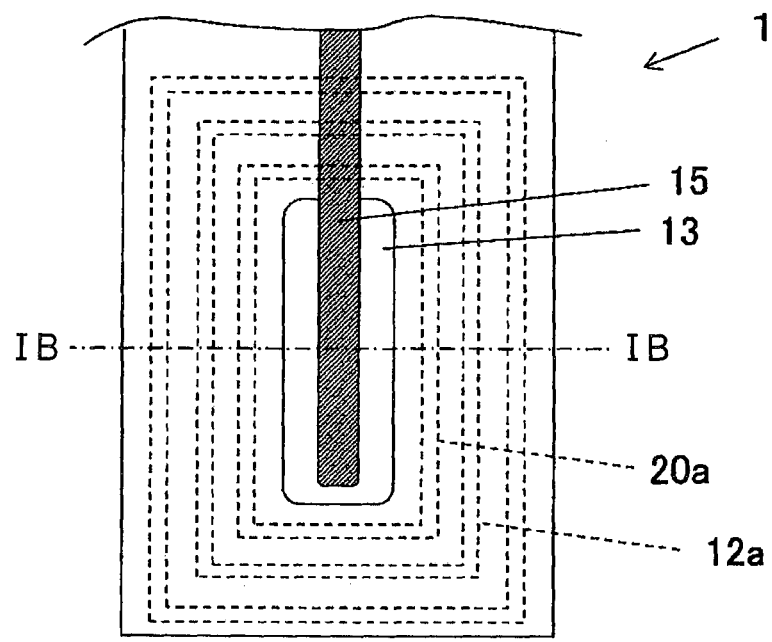
Figure 1B:
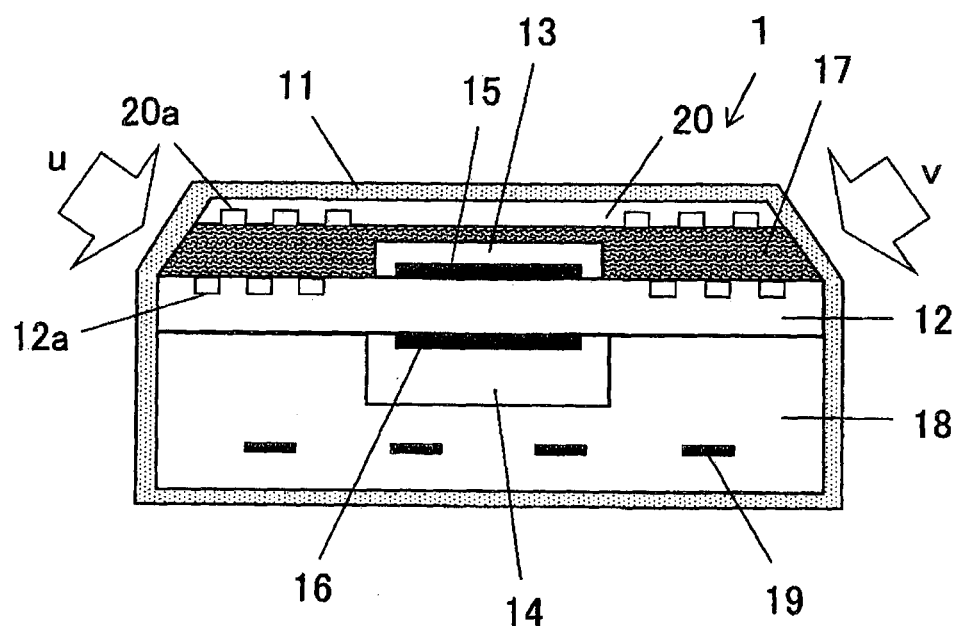

FIGS. 1A and 1B show the structure of a gas sensor element 1 that is included in a gas sensor according to this embodiment. The gas sensor is configured to enclose the gas sensor element 1 in a housing, for example. Gas whose concentration is measured by the gas sensor is oxygen, for example. However, the target gas, which is the gas to be measured, may be a gas other than oxygen.

The gas sensor element 1 includes a protective layer 11, a solid electrolyte body 12, a target gas chamber 13, a reference gas chamber 14, a target gas side electrode (first electrode) 15, a reference gas side electrode (second electrode) 16, a diffusion layer 17, a heater substrate 18, a heater 19, and a shielding layer 20.

The plate-shaped heater substrate 18, the solid electrolyte body 12, the diffusion layer 17, and the shielding layer 20 are laminated from the bottom to the top in this order. The target gas chamber 13 is a rectangular space that has a major central axis in a central part on an interface side with the solid electrolyte body 12 of the diffusion layer 17 in a plan view and is formed as a concave space that is depressed from the interface side with the solid electrolyte body 12 toward an inner side of the diffusion layer 17. The reference gas chamber 14 is a rectangular space that has a major central axis in the same position or in the approximately same position as the major central axis described above in a central part on an interface side with the solid electrolyte body 12 of the heater substrate 18 in a plan view and is formed a concave space that is depressed from the interface side with the solid electrolyte body 12 toward an inner side of the heater substrate 18. The target gas side electrode 15 is provided to come into contact with a surface of the solid electrolyte body 12 in the target gas chamber 13. The reference gas side electrode 16 is provided to come into contact with the surface of the solid electrolyte body 12 in the reference gas chamber 14. The solid electrolyte body 12 is held between the target gas side electrode 15 and the reference gas side electrode 16. As shown in FIG. 1A, the target gas side electrode 15 is drawn out of the gas sensor element 1 in a manner to extend linearly in a longitudinal direction, and the reference gas side electrode 16 is also drawn out of the gas sensor element 1 in a manner to extend in the same direction in a plan view.

The heater 19 is embedded in a lower part of the heater substrate 18. The protective layer 11 is provided to cover a circumference of the entire laminate described above. Although not shown, windows are provided to two sides of the protective layer 11 that do not intersect with the target gas side electrode 15 and the reference gas side electrode 16. These windows are provided to take a gas including the target gas into the diffusion layer 17 as shown with arrows u, v. The sides of the protective layer 11 that are provided with the windows and the diffusion layer 17 are trimmed in a tapered shape so as to face an upstream side from which the gas including the target gas is supplied.

The solid electrolyte body 12 is made of stabilized zirconia (YSZ) in which yttria ($Y_2O_3$) and the like are blended in zirconia ($ZrO_2$), for example. The protective layer 11, the diffusion layer 17, the heater substrate 18, and the shielding layer 20 are made of alumina ($Al_2O_3$), for example. The target gas side electrode 15 and the reference gas side electrode 16 are made of platinum (Pt), for example. The diffusion layer 17 is formed as a porous body.

One or more concave sections 12a that are depressed from an interface side with the diffusion layer 17 toward an inner side of the solid electrolyte body 12 are provided in the solid electrolyte body 12. One or more concave sections 20a that are depressed from an interface side with the diffusion layer 17 toward an inner side of the shielding layer 20 are provided in the shielding layer 20. For example, the concave section 12a is formed such that a connection surface of the solid electrolyte body 12 with respect to the interface with the diffusion layer 17 is orthogonal to the interface, while the concave section 20a is formed such that a connection surface of the shielding layer 20 with respect to the interface with the diffusion layer 17 is orthogonal to the interface. For example, as shown in FIG. 1A, the concave section 12a and the concave section 20a are provided to surround the circumference of the target gas chamber 13 in a plan view. In addition, the concave section 12a and the concave section 20a are provided so as not to overlap with each other in a plan view, for example.

In producing the gas sensor element 1 structured as above, the concave sections 12a, 20a are formed by cutting sheets for the solid electrolyte body 12 and the shielding layer 20 when the sheets are formed before firing. Then, the concave sections 12a, 20a are completed by firing after a normal laminating process. In the normal laminating process, the structure of the entire laminate structure except the protective layer 11 is fired, and the protective layer 11 is then dipped on the outer side of the fired laminate structure and fired at a lower temperature than a firing temperature of the entire laminate structure.

Next, operation of the gas sensor element 1 that is structured above will be described.

The gas sensor element 1 is arranged so as to be exposed to an exhaust gas flowing through an exhaust gas passage of a vehicle, for example. The protective layer 11 protects the inside of the gas sensor element 1 from the surrounding exhaust gas by protecting from a thermal shock and trapping unnecessary particles in an atmosphere. The exhaust as a gas containing the target gas is taken into the diffusion layer 17 from the windows of the protective layer 11. Because the diffusion layer 17 is the porous body, it functions as a resistance layer. A solution that contains a soluble poisoning component may be included in the exhaust gas. While the target gas passes through the porous body toward the target gas chamber, the solution containing the poisoning component is directed to the concave section 12a and the concave section 20a by a capillarity phenomenon as it permeates, the diffusion layer 17.

Meanwhile, the heater substrate 18 increases the temperature around the target gas side electrode 15 and the reference gas side electrode 16 by heating with the heater 19. When the target gas comes into contact with the target gas side electrode 15 and a reference gas of atmospheric air, for example, comes into contact with the reference gas side electrode 16, an electrical current that corresponds to a difference in oxygen concentration between the target gas and the reference gas flows between the target gas side electrode 15 and the reference gas side electrode 16 through the solid electrolyte body 12. Accordingly, the oxygen concentration of the target gas is detected.

Figure 2:
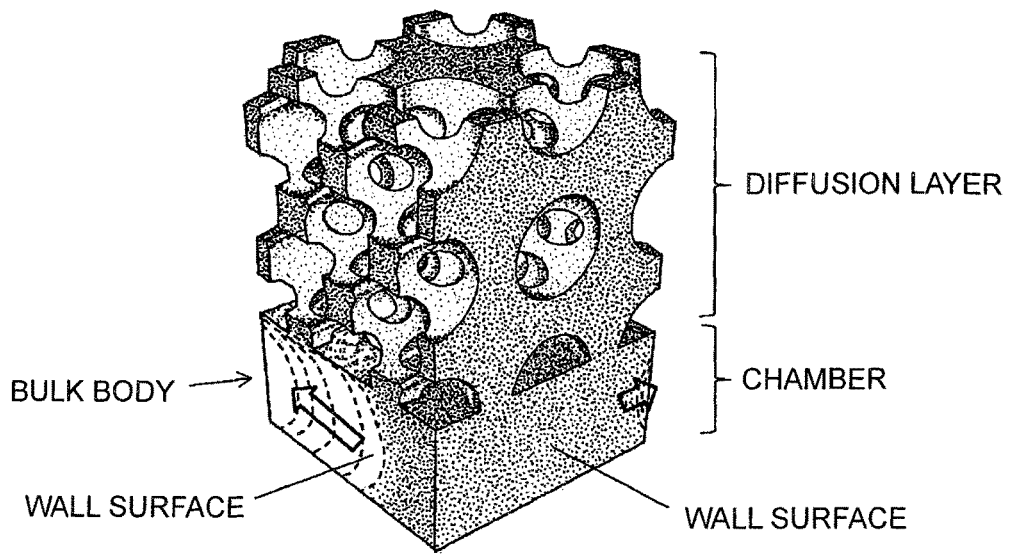
FIG. 2 shows the embodiment of the present invention which shows a simulation result of infusing behavior of water from a diffusion layer to a chamber.

Next, a description is made on a condition in which the solution containing the poisoning component is directed to a concave section through the diffusion layer. FIG. 2 shows a simulation result of the behavior of water injected into the diffusion layer with respect to a chamber space. The simulation was performed by modeling the structure in which the diffusion layer is provided on top of an alumina bulk body and the chamber (an outer horizontal space of the bulk body in FIG. 2 is designated as the chamber) as the concave section is provided in the bulk body. A wall surface of the chamber is orthogonal to an upper surface of the bulk body. This corresponds to a fact that a connection surface of the concave section with respect to an interface between a layer provided with the concave section and the diffusion layer is orthogonal to the interface.

Dotted parts in FIG. 2 contain a substantial amount of water, and it can be understood that water permeates the porous body of the diffusion layer and sufficiently reaches the wall surface of the chamber. Injected water is absorbed by a porous space of the diffusion layer by the capillarity phenomenon. Meanwhile, because the wall surface of the chamber is orthogonal to the upper surface of the bulk body, a vector component for discharging water from the porous space to the chamber as an opened, space becomes extremely large. Accordingly, water seeps down the wall surface such that it is discharged from the diffusion layer to the chamber. This seeping effect of water into the chamber is increased as an angle formed by the wall surface of the chamber (thus the connection surface of the concave section) to the upper surface (thus the interface) of the bulk body approximates 90 degrees. Water reaches the wall surface of the chamber under no influence of its gravity. Therefore, the same simulation result can be obtained even when the chamber is present in a position other than that under the diffusion layer, such as above the diffusion layer. In the wall surface of the chamber, the amount of water gradually decreases in a direction of an arrow. Consequently, it was confirmed that water from the diffusion layer seeped into the chamber space and expanded through the wall surface of the chamber.

Next, the verification of an effect of providing the concave section will be described.

Figure 3A:
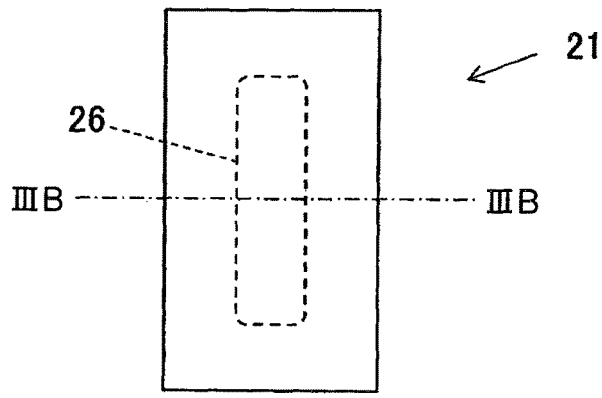
Figure 3B:
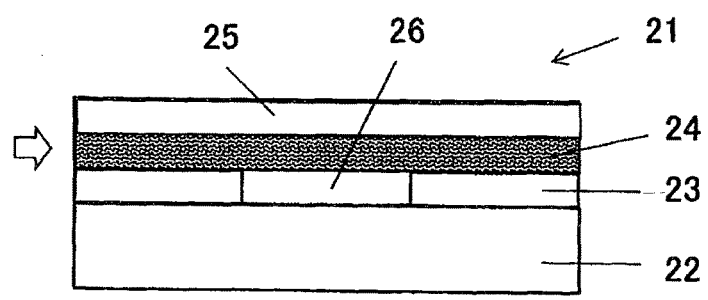

FIGS. 3A, 3B show the structure of a test piece 21 that was used to verify the effect of the concave section.

The test piece 21 is structured such that an alumina layer 22, an alumina layer 23, a diffusion layer 24, and an alumina layer 25 are laminated from the bottom to the top in this order. A chamber 26 formed of a concave section is provided in the alumina layer 23. The chamber 26 contacts the alumina layer 22 at a lower layer side and the diffusion layer 24 at an upper layer side. Accordingly, a wall surface of the chamber 26 is configured by a side wall of the alumina layer 23, and a bottom surface of the chamber 26 is configured by an upper surface of the alumina layer 22.

A cycle test (acceleration test) for repeating a cycle in which water containing poisoning element ions was dropped from a side surface of the diffusion layer 24 to the test piece 21 as shown by an arrow in FIG. 3B and was then dried in the atmosphere for a plurality of times was performed. FIG. 4A shows a surface analysis result obtained by an electron probe micro analyzer (EPMA) that a poisoning element 30 is deposited in the chamber 26 with an increase in the number of cycles. As a result, it was confirmed that the poisoning element 30 was hardly deposited at first in an area at the bottom of the chamber 26 that was surrounded by a dashed-dotted line; however, the deposition of the poisoning element 30 progressed with the increase in the number of cycles.

FIG. 4B is a scanning electron microscopic (SEM) picture that shows a state of deposition of the poisoning element 30. The poisoning element 30 was deposited significantly at the end of the chamber. In addition, the results shown in FIGS. 4A, 4B were obtained in a case where the test piece 21 faced either upward or downward and in a case where the test piece 21 was inclined to a vertical direction, that is, regardless of the orientation of the test piece 21.

As described above, the gas sensor element 1 according to this embodiment catches a soluble poisoning substance contained in the exhaust gas with the concave section provided in at least one of the layers that come into contact with the lower layer and upper layer of the diffusion layer. In other words, the soluble poisoning substance can be caught by the concave section that is provided in at least one of the shielding layer 20 and the solid electrolyte body 12 that come into contact with the diffusion layer 17 and hold the diffusion layer 17 therebetween. Accordingly, it is possible to remove adverse influence the target gas that responds to the electrode on the atmosphere. More specifically, the poisoning substance in the exhaust gas or the poisoning substance adhered to the protective layer 11 dissolves in water supplied by the surrounding environment of the gas sensor element 1, permeates the diffusion layer 17 by the capillarity phenomenon, and is caught and retained in the concave sections 12a, 20a as open spaces. Accordingly, the poisoning substance is not retained in an area from the surface of the protective layer 11 to the inside of the diffusion layer 17 or does not reach the target gas chamber 13 to soil a target gas electrode, and thus a measuring environment is not damaged. Therefore, because there is no deterioration with time, which could be caused by the poisoning, it is possible to restrict occurrence of abnormality that may be set by the regulation of an exhaust gas system. In addition, because the frequency of part replacement caused by degraded functions of the gas sensor element is reduced, it is significantly advantageous in terms of cost. Furthermore, because the accumulation amount of the poisoning substance that adheres to the inner surface of the concave section is much smaller than a volume of the concave section, a life cycle of the gas sensor is not shortened by the excessive accumulation of the poisoning substance. Moreover, it is possible to reduce anxiety and gain trust of consumers.

It should be noted that only one of the concave section 12a and the concave section 20a may be provided in the gas sensor element 1 in FIG. 1. In addition, like the diffusion layer 17 that has two paths of a take-in path in the arrow u side and a take-in path in the arrow v side in FIG. 1, for example, plural gas diffusion paths can be provided separately. For example, if at least one concave section is provided in each of the gas diffusion paths, the poisoning substance that permeates the diffusion layer 17 can be retained uniformly.

Figure 5A:
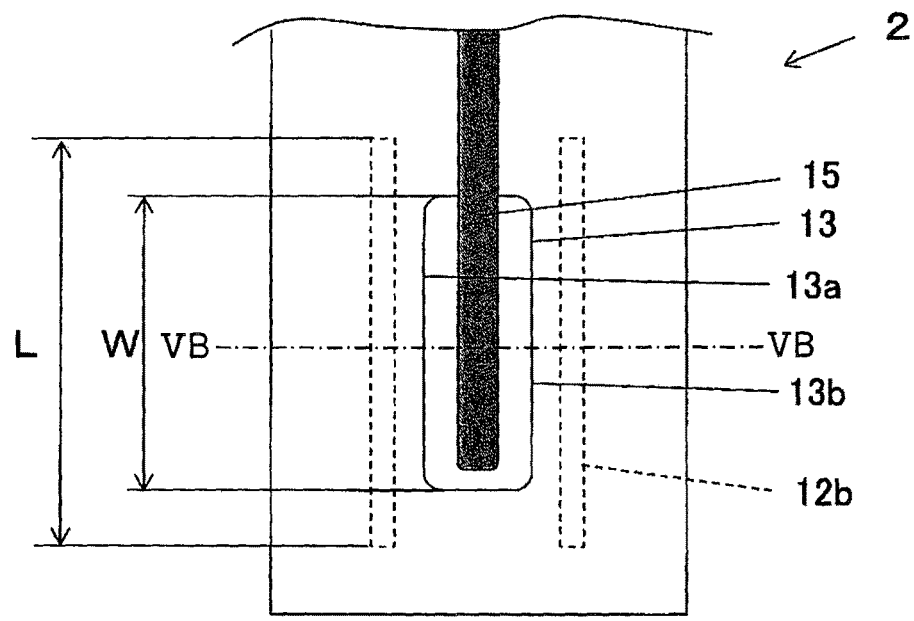
Figure 5B:
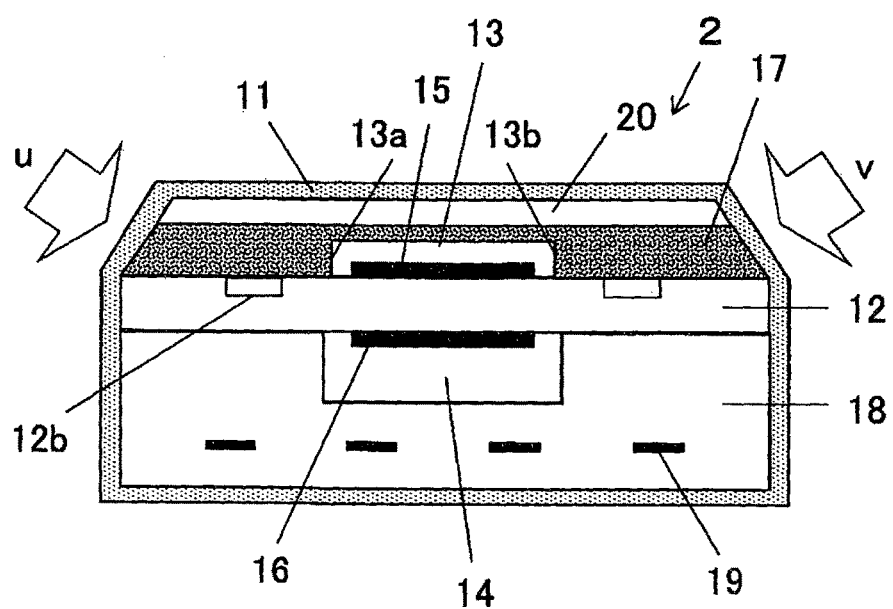

FIGS. 5A, 5B show the structure of a gas sensor element 2 according to a first modification. Components of the gas sensor element 2 that correspond to those of the gas sensor element 1 in FIG. 1 are denoted by the same reference numerals, and their description is not repeated.

The gas sensor element 2 is configured such that a strip-shaped concave section 12b is provided on the diffusion layer 17 side in the solid electrolyte body 12. The strip-shaped concave section 12b is arranged in both of two exhaust gas take-in sides and is located between the target gas chamber 13 and the exhaust gas take-in side, (positions near exhaust gas take-in points) that are away from the target gas chamber 13. More specifically, the two concave sections 12b are provided: one of which corresponds to the gas diffusion path provided from a chamber side wall 13a that faces one of the exhaust gas take-in sides of the target gas chamber 13 to the target gas chamber 13 (that is, the take-in path in the arrow u side); and the other of which corresponds to the gas diffusion path provided from a chamber side wall 13b that faces the other of the exhaust gas take-in sides of the target gas chamber 13 to the target gas chamber 13 (that is, the take-in path in the arrow v side). The gas sensor element 2 has the same structure as the gas sensor element 1 except the above.

As shown in FIG. 5A, the concave sections 12b are provided in parallel or substantially in parallel with the chamber side walls 13a, 13b that face the exhaust gas take-in sides of the target gas chamber 13, for example. The gas sensor element 2 is not provided with the concave section on the outer side of the side wall of the target gas chamber 13 that is orthogonal to the chamber side walls 13a, 13b. However, when the exhaust gas take-in sides are seen from the target gas chamber 13 in a plan view, the areas covered by the concave sections 12b in the parallel direction with the chamber side walls 13a, 13b correspond to a range L. A range W that corresponds to a width of each of the chamber side walls 13a, 13b of the target gas chamber 13 is contained in this range L. In other words, when the target gas take-in side is seen from the target gas chamber 13 in a plan view, and the length of the wall surface of the target gas chamber 13 that faces the target gas take-in side is set as a chamber width, the length of the concave section 12b in a direction of the chamber width is longer than the chamber width of the target gas chamber 13. In this case, an exhaust gas take-in direction is present on the plane in the same plan view. When the range W is contained in the range L, there is hardly any poisoning substance that goes around and permeates the target gas chamber 13 in the orthogonal direction to the chamber side walls 13a, 13b, and thus it is difficult for the poisoning substance to reach the target gas chamber 13 without passing through the diffusion area where the concave sections 12b are located. Therefore, a probability of the poisoning substance that passes through the diffusion layer to be caught in the concave section before reaching the target gas chamber 13 is increased. In the gas sensor element 1 of FIG. 1, the concave sections 12a, 20a are arranged such that the range W is inevitably contained in the range L. Even if the range W is not contained in the range L, a probability of the concave sections 12b to catch the poisoning substance is increased as long as the range L is substantially the same as the range W.

In FIG. 5B, two or more of the concave sections 12b may be provided for each of the take-in passages that are shown with the arrows u, v. In this case, when each of the gas take-in sides is seen from the target gas chamber 13, the ranges of the concave sections 12b for each of the take-in paths in parallel with the chamber side walls 13a, 13b in a plan view are formed in series along the parallel direction, thereby forming a total range L (the same concept as the total range L in FIGS. 7A and 8A described below). In this case, if the range W is contained in the range L, the possibility of the concave sections 12b to catch the poisoning substance is increased similarly.

FIG. 5B shows a shape of the wall surface of the concave section 12b that is perpendicular to the interface with the diffusion layer 17. Because a three-phase interface is formed, it is possible to improve an effect of trapping the poisoning substance.

An effect of poisoning resistance of the gas sensor element 2, which was configured as above, was verified. Similar to the test piece 21 described above, the cycle test (acceleration test) for repeating a cycle in which a solution with the dissolved poisoning substance was brought into contact with (was injected into) a portion of the diffusion layer 17 positioned at the center in the longitudinal direction of the chamber from the outside of the element by a micro syringe and was then dried for the plurality of times was performed for the verification.

Figure 6A:
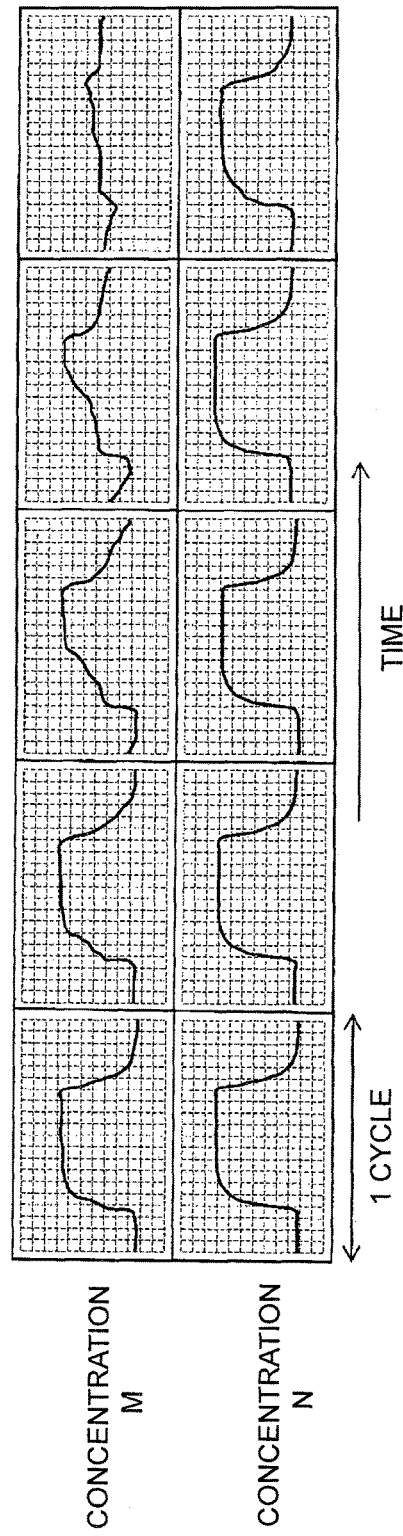
FIG. 6A is a graph for showing a change in a gas response property in a cycle test for the gas sensor element of FIGS. 5A, 5B along with a comparison with a conventional gas sensor element.

FIG. 6A shows a change in a gas response property per cycle when the cycle test was conducted for five cycles. An upper stage of FIG. 6A shows a gas response property M of a conventional gas sensor element that is not provided with the concave section, and a lower stage thereof shows the gas response property N of the gas sensor element 2. A horizontal axis represents time, and a vertical axis represents detected concentration of the target gas. It is shown that response delays accumulate and a response waveform is collapsed as the number of cycles increases in the gas response property M. On the other hand, regardless of the number of cycles, the gas response property N exhibits stable and sharp responses. It was confirmed from this result that the structure of the gas sensor element 2 sufficiently functioned to catch the poisoning substance and effective to maintain a sensor characteristic.

Figure 6B:
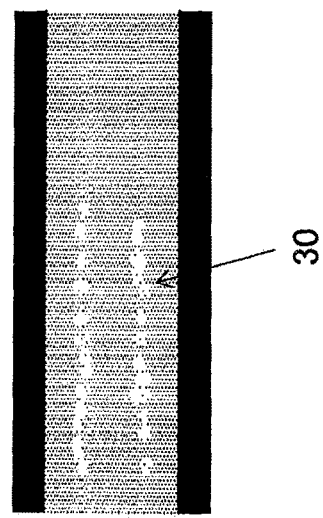
FIG. 6B shows the EPMA result after the cycle test.

FIG. 6B shows a surface analysis result by the EPMA after the cycle test. In the analysis result, the deposition of the poisoning element 30 is clearly confirmed, and thus the result supports a fact that the gas sensor element 2 can sufficiently catch the poisoning substance.

Figure 7A:
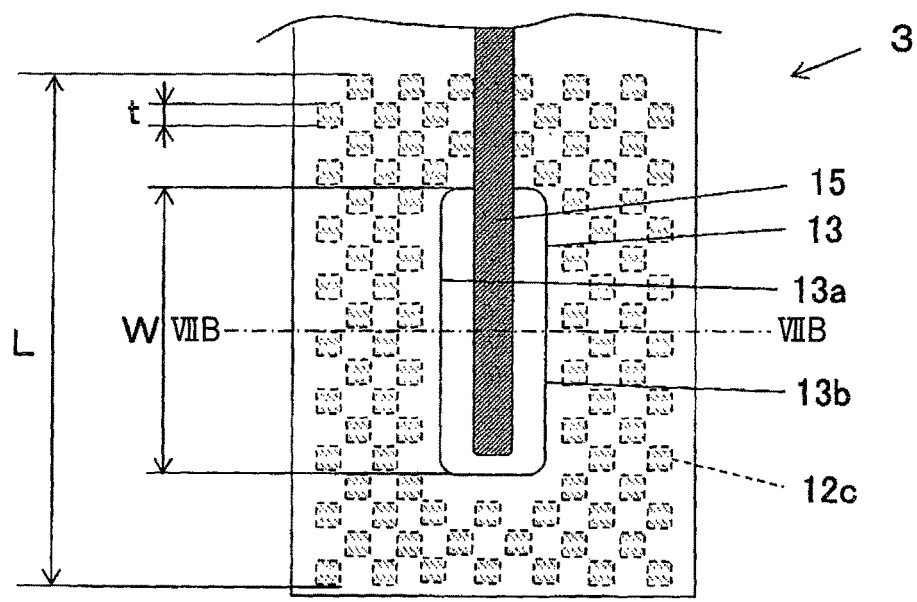
Figure 7B:
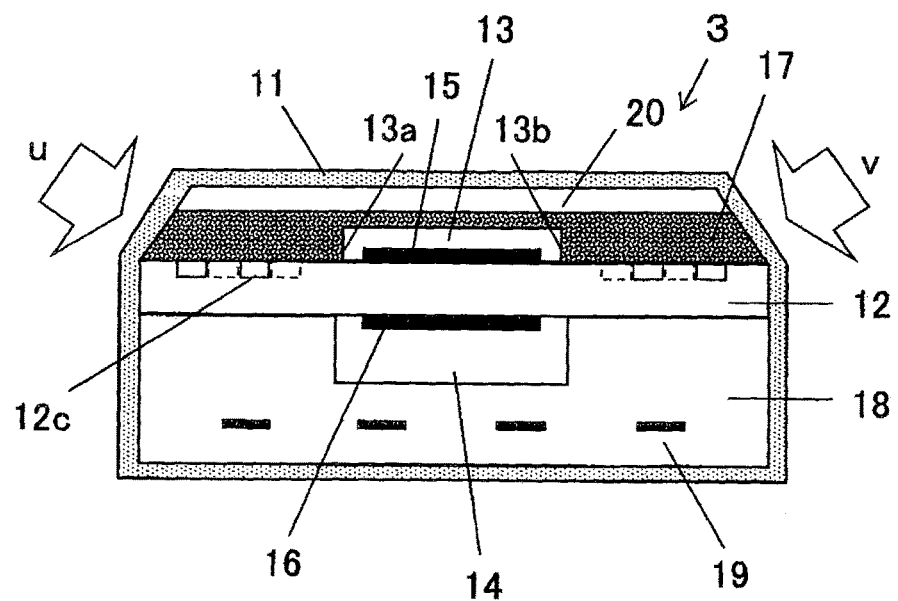

FIGS. 7A, 7B show the structure of a gas sensor element 3 according to a second modification. Components of the gas sensor element 3 that correspond to those of the gas sensor element 1 are denoted by the same reference numerals, and their description is not repeated.

The gas sensor element 3 is provided with a plurality of concave sections 12c on the surface of the solid electrolyte body 12 that comes into contact with the diffusion layer 17. The concave sections 12c are arranged around the target gas chamber 13 in a plan view.

Each of the concave sections 12c has a range t in the parallel direction with the chamber side walls 13a, 13b that respectively correspond to the take-in path shown with the arrow u and the take-in path shown with the arrow v. When each of the gas take-in sides is seen from the target gas chamber 13, the concave sections 12c are arranged at specified intervals in the parallel direction, and the ranges in which the concave sections 12c are arranged correspond to the range L. This range L contains the range W that is the width of the chamber side walls 13a, 13b.

FIG. 7B shows an example in which an angle of the wall surface of the concave section 12c to the interface of the solid electrolyte body 12 with the diffusion layer 17 is 90 degrees or approximately 90 degrees.

Figure 8A:
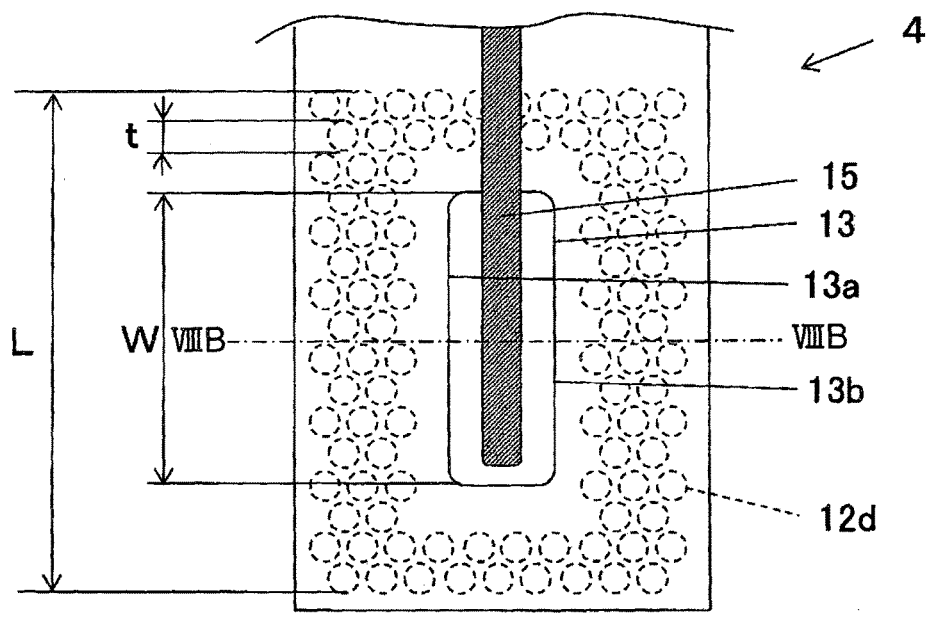
Figure 8B:
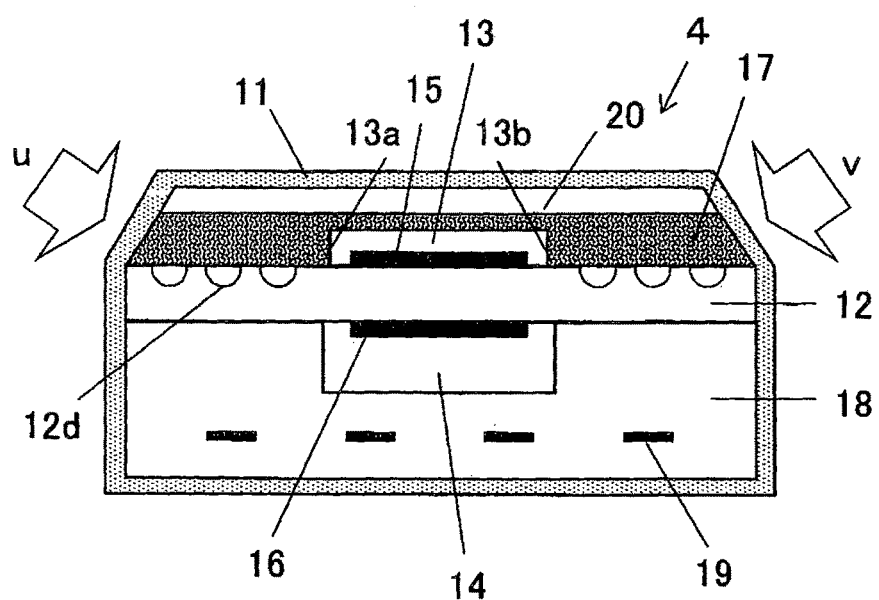

FIGS. 8A, 8B show the structure of a gas sensor element 4 according to a third modification. Components of the gas sensor element 4 that correspond to those of the gas sensor element 1 are denoted by the same reference numerals, and their description is not repeated.

The gas sensor element 4 is provided with a plurality of concave sections 12d on the surface of the solid electrolyte body 12 that comes into contact with the diffusion layer 17. The concave sections 12d are arranged around the target gas chamber 13 in a plan view.

Each of the concave sections 12d has a range t in the parallel direction with the chamber side walls 13a, 13b that respectively correspond to the take-in path shown with the arrow u and the take-in path shown with the arrow v. When each of the gas take-in sides is seen from the target gas chamber 13, the concave sections 12d are arranged at specified intervals in the parallel direction, and the ranges in which the concave sections 12d are arranged correspond to the range L. This range L contains the range W that is the width of the chamber side walls 13a, 13b.

The present invention can be applied to a gas sensor or the like that is used for combustion control of an exhaust system in a vehicle.

The invention claimed is:

1. A gas sensor element for detecting a concentration of a target gas comprising:
    a solid electrolyte body;
    a target gas chamber to which the target gas is introduced;
    a reference gas chamber to which a reference gas that serves as basis of the concentration of the target gas is introduced;
    a first electrode provided in the target gas chamber so as to come into contact with the solid electrolyte body;
    a second electrode provided in the reference gas chamber so as to come into contact with the solid electrolyte body, the second electrode being provided to hold the solid electrolyte body between the first electrode and the second electrode;
    a diffusion layer arranged to come into contact with the solid electrolyte body and configured to deliver the target gas to the target gas chamber; and
    a shielding layer arranged to come into contact with the diffusion layer such that the diffusion layer is arranged between the solid electrolyte body and the shielding layer, wherein at least one of the solid electrolyte body and the shielding layer is provided with a concave section that is depressed from a surface contacting the diffusion layer,
    wherein, when a target gas take-in side that takes in the target gas is seen from the target gas chamber in a plan view, and a length of a wall surface of the target gas chamber that faces the target gas take-in side is set as a chamber width, a range of the concave section in a direction of the chamber width is at least as long as the chamber width, and
    wherein the concave section is provided in a strip shape in parallel with a side wall of the target gas chamber that faces the target gas take-in side in plan view, a length of the strip shape being larger than a length of the side wall of the target gas chamber.

2. The gas sensor element according to claim 1, wherein a surface of the diffusion layer in the target gas take-in side is trimmed in a tapered shape to face an upstream side of the target gas.

3. The gas sensor element according to claim 1, wherein a wall surface of the concave section is perpendicular to an interface thereof with the diffusion layer.

4. The gas sensor element according to claim 1, wherein the target gas chamber is a rectangular space that has a major central axis in a central part on an interface side with the solid electrolyte body of the diffusion layer in a plan view and is formed to be depressed from the interface side with the solid electrolyte body toward an inner side of the diffusion layer.

5. The gas sensor element according to claim 1, wherein the concave section is provided to surround the target gas chamber in a plan view.

6. The gas sensor element according to claim 5, wherein the concave section is provided in both of the solid electrolyte body and the shielding layer, and the concave sections are provided not to overlap with each other in the plan view.

7. A gas sensor comprising the gas sensor element according to claim 1.

8. The gas sensor element according to claim 1, wherein the concave section is provided in both of the solid electrolyte body and the shielding layer, and the concave sections are provided not to overlap with each other in the plan view.

* * * * *